United States Patent [19]

Malherbe et al.

[11] 4,154,722

[45] May 15, 1979

[54] POLYALKYLPIPERIDINYL ESTERS OF DIAZOCARBOXYLIC ACID AND THEIR USE FOR STABILIZING POLYMERS

[75] Inventors: Roger Malherbe, Muttenz; Michael Rasberger, Riehen, both of Switzerland

[73] Assignee: Ciba-Geigy Corporation, Ardsley, N.Y.

[21] Appl. No.: 807,960

[22] Filed: Jun. 20, 1977

[30] Foreign Application Priority Data

Jun. 23, 1976 [CH] Switzerland .......................... 8015/76

[51] Int. Cl.$^2$ ................. C07C 113/02; C07D 203/18; C08K 5/10; C08K 5/20
[52] U.S. Cl. .......................... 260/45.8 N; 260/45.8 R; 260/141; 260/156; 260/239 AA; 546/190
[58] Field of Search ....... 260/141 D, 141 H, 239 AA, 260/293.81, 293.82, 45.8 N, 45.8 R

[56] References Cited

U.S. PATENT DOCUMENTS 3,440,239  4/1969  Harvey ............................ 260/141 D
3,509,131  4/1970  Church et al. ............... 260/239 AA

OTHER PUBLICATIONS

Holt et al., Chemical Abstracts, vol. 79, #54269u (1973).
Murayama et al. (I), Chemical Abstracts, vol. 72, #67726w (1970).
Murayama et al. (II), Chemical Abstracts, vol. 83, #60490h (1975).
Matsui et al., Chemical Abstracts, vol. 77, #20730f (1972).

*Primary Examiner*—Floyd D. Higel
*Attorney, Agent, or Firm*—Vincent J. Cavalieri

[57] ABSTRACT

Polyalkylpiperidinyl esters of diazocarboxylic acids are prepared, which compounds protect organic polymers against UV light degradation. The light stabilizers have the ability to react with the organic polymeric substrates thus making the piperidinyl esters migration and extraction resistant. Polymers which may be stabilized with the compounds of this invention include polypropylene, polyethylene, polystyrene and polyamides.

14 Claims, No Drawings

POLYALKYLPIPERIDINYL ESTERS OF DIAZOCARBOXYLIC ACID AND THEIR USE FOR STABILIZING POLYMERS

The invention relates to the stabilisation of organic polymers against light degradation by means of an addition reaction of derivatives of sterically hindered alkyl-piperidines with the polymer. For this purpose, new piperidine derivatives containing a diazocarboxylic acid radical are used.

Sterically hindered polyalkylpiperidines are known to be effective light stabilisers for plastics, above all those piperidines which are substituted in the 4-position. Examples of these are the derivatives of polyalkylated 4-hydroxy-piperidines, such as are described in DT-OS Nos. 1,929,928 and 2,258,752, of the derivatives of polyalkylated 4-aminopiperidines, such as are described in DT-OS Nos. 2,040,975 and 2,349,962. An example of piperidine derivatives of this type is bis-(2,2,6,6-tetramethylpiperidin-4-yl) sebacate which is used industrially as a light stabiliser for plastics, above all for polyolefines.

As in the case of most plastic additives, there is also a danger in the case of the light stabilisers mentioned that the light stabiliser can partially migrate out or volatilise when the plastic is used for a prolonged period, so that the stabilising activity gradually diminishes. Particularly high losses of activity can arise on extraction. This is the case when the plastic is in contact with liquids, for example in the case of plastic bottles or on exposure to the weather. For certain fields of application a greater permanence of the activity is thus desirable or even necessary. Such greater permanence should be expected if the light stabiliser is chemically bonded to the polymer, but this has not generally been feasible with the polyalkylpiperidine light stabilisers hitherto known.

It has now been found that organic polymers can be protected against light degradation by reacting them with diazocarboxylic acid derivatives of polyalkylpiperidines of the formula I

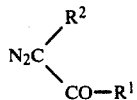

in which $R^1$ is a radical of the formula II or III

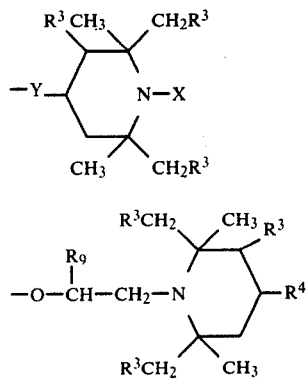

and $R^2$ represents hydrogen or one of the groups —CHO, —CN, —NO$_2$, —COR$^1$, —COR$^5$, —SO$_2$R$^6$, —COOR$^7$, —CONH$_2$, —CONHR$^{17}$, —CON(R$^{17}$)$_2$, —P(O)(C$_6$H$_5$)$_2$ or —P(O)(OR$^{18}$)$_2$ and, in these formulae, X denotes H, O·, alkyl with 1–12 C atoms, alkenyl with 3–6 C atoms, alkinyl with 3–6 C atoms, alkoxyalkyl with 3–10 C atoms, phenylalkyl with 7–9 C atoms, a 2,3-epoxypropyl group or one of the groups —CH$_2$COOR$^8$, —CH$_2$CH$_2$COOR$^8$, —CH$_2$CH(R$^9$)—OR$^{10}$, —COR$^{11}$, —COOR$^{12}$ or —CONHR$^{13}$, Y denotes oxygen, NH or N-alkyl with 1–4 C atoms, $R^3$ denotes H or alkyl with 1–4 C atoms, $R^4$ denotes H, —OR$^{14}$ or —N(R$^{15}$)(R$^{16}$), $R^5$ and $R^6$ denote alkyl with 1–18 C atoms, cyclohexyl, aryl with 6–10 C atoms, which can be substituted by chlorine or C$_1$–C$_8$ alkyl, phenylalkyl with 7–9 C atoms or a phenyl or phenylalkyl radical which is substituted by one or two alkyl groups with 1–4 C atoms and/or by hydroxyl, or a group of the formula —CH$_2$COR$^1$ or —CH$_2$COOR$^{12}$, $R^7$ denotes alkyl with 1–18 C atoms, alkenyl with 3–6 C atoms, alkinyl with 3–6 C atoms, cycloalkyl with 5–12 C atoms, phenyl, phenylalkyl with 7–9 C atoms or alkylphenyl with 7–14 C atoms, $R^8$ denotes alkyl with 1–18 C atoms, alkenyl with 3–6 C atoms, phenyl, benzyl or cyclohexyl, $R^9$ denotes H, methyl or phenyl, $R^{10}$ denotes H, C$_1$–C$_{18}$ alkyl, C$_5$–C$_{12}$ cycloalkyl, C$_7$–C$_{14}$ aralkyl, C$_3$–C$_6$ alkenyl, C$_3$–C$_6$ alkinyl or an aliphatic, aromatic, araliphatic or cycloaliphatic acyl group with up to 18 C atoms, wherein the aromatic part can be substituted by halogen, alkoxy with 1—4 C atoms, alkyl with 1–4 C atoms and/or hydroxyl, $R^{11}$ denotes H, alkyl with 1–6 C atoms or alkenyl with 2–4 C atoms, $R^{12}$ denotes alkyl with 1–12 C atoms, phenyl, benzyl or cyclohexyl, $R^{13}$ denotes alkyl with 1–12 C atoms, aryl with 6–10 C atoms which can be substituted by chlorine or alkyl with 1–8 C atoms, phenylalkyl with 7–9 C atoms or cyclohexyl, $R^{14}$ denotes alkyl with 1–18 C atoms, alkenyl with 3–6 C atoms, alkinyl with 3–6 C atoms, benzyl, 2-cyanoethyl, an aliphatic, cycloaliphatic, aromatic or araliphatic acyl group with up to 18 C atoms, which can be substituted in the aromatic part by halogen, alkoxy with 1–4 C atoms, alkyl with 1–4 C atoms and/or hydroxyl, $R^{15}$ denotes alkyl with 1–18 C atoms, alkenyl with 3–6 C atoms or phenylalkyl with 7–9 C atoms, $R^{16}$ denotes an aliphatic, cycloaliphatic, aromatic or araliphatic acyl group with up to 18 C atoms, which can be substituted in the aromatic part by halogen, alkoxy with 1–4 C atoms, alkyl with 1–4 C atoms and/or hydroxyl, $R^{17}$ denotes alkyl with 1–12 C atoms, cyclohexyl, benzyl or phenyl and $R^{18}$ denotes alkyl with 1–18 C atoms, aryl with 6–10 C atoms, which can be substituted by chlorine or alkyl with 1–8 C atoms, or phenylalkyl with 7–9 C atoms.

In the meaning of alkyl with 1–4 C atoms, $R^3$ can be an unbranched or branched alkyl radical, for example ethyl, propyl, butyl, isopropyl or sec.-butyl, but preferably methyl. The same applies to Y in the meaning of N-alkyl. Furthermore, in the meaning of alkyl with 1–6 C atoms, $R^{11}$ can be, for example, a pentyl or 2-ethylbutyl group.

Furthermore, in the meaning of alkyl with 1–12 C atoms, X, $R^{12}$, $R^{13}$ and $R^{17}$ can be for example, n-octyl, 2-ethylhexyl, iso-nonyl, n-decyl or n-dodecyl.

Furthermore, in the meaning of alkyl with 1–18 C atoms, $R^5$, $R^6$, $R^7$, $R^8$, $R^{14}$, $R^{15}$ and $R^{18}$ can be, for example, tetradecyl, hexadecyl or octadecyl.

If X, $R^7$, $R^8$, $R^{14}$ or $R^{15}$ denote alkenyl with 3–6 C atoms, these can be, for example, allyl, methallyl, 2-butenyl or 2-hexenyl.

In the meaning of alkenyl with 2–4 C atoms, $R^{11}$ can be vinyl, propenyl or butenyl.

In the meaning of alkinyl with 3–6 C atoms, X, $R^7$ and $R^{14}$ can be, for example, propargyl, 2-butinyl or 2-hexinyl.

In the meaning of alkoxyalkyl with 3–10 C atoms, X can be, for example, methoxyethyl, isopropoxyethyl, hexyloxyethyl or butoxymethyl. Preferably it is a 2-alkoxyethyl radical.

If $R^5$, $R^6$, $R^{13}$ or $R^{18}$ denote aryl with 6–10 C atoms, which can be substituted by chlorine or alkyl with 1–8 C atoms, this can be, for example, phenyl, chlorophenyl, 2,4-dichlorophenyl, naphthyl, 4-chloro-1-naphthyl, tolyl, 4-tert.-butylphenyl or 4-octylphenyl.

If X, $R^5$, $R^6$, $R^7$, $R^{13}$, $R^{15}$ or $R^{18}$ denote phenylalkyl with 7–9 C atoms, this can be, for example, benzyl, phenylethyl, methylbenzyl or dimethylbenzyl.

$R^5$ and $R^6$ can also be a phenylalkyl group which is substituted by alkyl groups and/or hydroxyl groups, such as, for example, 4-tert.-butylbenzyl, 3,5-dimethyl-4-hydroxybenzyl, 4-hydroxybenzyl or 2-(3,5-di-tert.-butyl-4-hydroxyphenyl)-ethyl.

If $R^7$ denotes cycloalkyl with 5–12 C atoms, this can be, for example, cyclopentyl, cyclohexyl, methylcyclohexyl, cyclooctyl or cyclododecyl.

In the meaning of alkylphenyl with 7–14 C atoms, $R^7$ can, for example, be p-tolyl, 3-isopropylphenyl, 4-tert.-butylphenyl or 4-octylphenyl.

If $R^{10}$, $R^{14}$ or $R^{16}$ is an aliphatic, aromatic, araliphatic or cycloaliphatic acyl group with up to 18 C atoms, wherein the aromatic part can be substituted by halogen, alkoxy, alkyl and/or hydroxyl, these can be, for example, a formyl, acetyl, propionyl, butyryl, hexanoyl, 2-ethylhexanoyl, isodecanoyl, dodecanoyl, stearoyl, acryl, crotonyl, oleyl, benzoyl, naphthoyl, 3-chlorobenzoyl, 4-methoxybenzoyl, 4-bromo-1-naphthoyl, 4-tert.-butylbenzoyl, 2,4-dichlorobenzoyl, 2-hydroxybenzoyl, 3,5-di-tert.-butyl-4-hydroxybenzoyl, phenylacetyl, β-phenylpropionyl, 4-chlorophenylacetyl, β-naphthylacetyl, 2-(3,5-di-tert.-butyl-4-hydroxyphenyl)-propionyl, hexahydrobenzoyl or decahydronaphthoyl radical.

The diazo compounds of the formula I are new compounds which act as light stabilisers even if they are not reacted with the polymer but only admixed. The reaction of the diazo compounds with the polymeric substrates is effected by heating to above 100° C. or by irradiation with light of short wavelengths. This forms a chemical bond between the stabiliser and the polymer, and this bond has the effect that the stabiliser is no longer extractable and can no longer migrate out of the polymer.

This heating can be carried out simultaneously with the processing for the purpose of shaping, many plastics being processed in the same temperature range, for example by hot pressing, extrusion or injection moulding.

The diazo compounds of the formula I can be prepared by various methods, such as are known in themselves for the preparation of α-diazocarboxylic acid derivatives. The most important of these methods are:

(a) Introduction of the diazo group into the α-methylene group by means of sulphonic acid azides, such as, for example, tosyl azide, in the presence of basic catalysts;

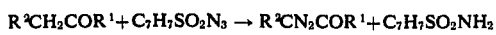
$R^2CH_2COR^1 + C_7H_7SO_2N_3 \rightarrow R^2CN_2COR^1 + C_7H_7SO_2NH_2$ (b) Diazotisation of α-aminocarboxylic acid derivatives:

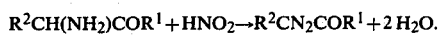
$R^2CH(NH_2)COR^1 + HNO_2 \rightarrow R^2CN_2COR^1 + 2H_2O$.

Examples of further known methods for introducing a diazo group into the α-position are the Forster reaction of α-ketoximes, the dehydrogenation of α-hydrazones by means of manganese dioxide, the Bamford-Stevens reaction of α-tosylhydrazones or the deacylation of N-nitroso-α-acylaminocarboxylic acid derivatives. Examples of the preparation of diazo compounds of the formula I are described in the subsequent text.

Because of accessibility and effectiveness, the following groups amongst the diazo compounds generally defined by formula I, are of particular interest:

1. Compounds of the formula I, in which $R^1$ is a radical of the formula II or III and $R^3$ denotes hydrogen or methyl, preferably hydrogen.

2. Compounds in which $R^1$ is a radical of the formula II wherein X represents hydrogen, alkyl with 1–8 C atoms, allyl, benzyl or one of the groups $-CH_2COOR^8$, $-CH_2CH_2COOR_8$, $-CH_2CH_2OR^{10}$ or $-COR^{11}$ and $R^8$ denotes alkyl with 1–12 C atoms, $R^{10}$ denotes H or alkanoyl with 1–18 C atoms and $R^{11}$ denotes alkyl with 1–3 C atoms, vinyl or propenyl.

3. Compounds in which $R^1$ is a radical of the formula III wherein $R^4$ represents hydrogen or $-OR^{14}$ and $R^{14}$ denotes an aliphatic acyl radical with 1–18 C atoms or a benzoyl radical.

4. Compounds in which $R^1$ is a radical of the formula II or III and $R^2$ denotes H, CN, $-COR^1$, $-COR^5$, $-SO_2R^6$ or $-COOR^7$ and $R^5$ denotes alkyl with 1–8 C atoms, phenyl, 4-hydroxy-3,5-di-tert.-butylphenyl or 2-(4-hydroxy-3,5-di-tert.-butylphenyl)-ethyl, $R^6$ denotes alkyl with 1–12 C atoms, phenyl or 4-hydroxy-3,5-di-tert.-butylbenzyl and $R^7$ denotes alkyl with 1–18 C atoms.

Amongst these, those compounds of the formula I are particularly preferred wherein $R^1$ is a radical of the formula II in which $R^3$ is hydrogen, X is hydrogen or methyl and Y is oxygen, or wherein $R^1$ is a radical of the formula III in which $R^3$ and $R^4$ are hydrogen, and wherein $R^2$ denotes hydrogen, $-CN$, $-COR^1$, $-COR^5$ or $-COOR^7$ and $R^5$ denotes alkyl with 1–6 C atoms or phenyl and $R^7$ denotes alkyl with 1–4 C atoms.

The following are examples of individual compounds of the formula I:
(1) 2,2,6,6-Tetramethyl-4-piperidinyl diazoacetate
(2) 3-Oxo-2-diazo-3-phenyl-propanoic acid (2,6-diethyl-1,2,5,6-tetramethyl-4-piperidinyl)-amide
(3) 2,2,6,6-Tetramethyl-4-piperidinyl 3-oxo-2-diazo-3-cyclohexyl-propanoate
(4) 1,2,2,6,6-Pentamethyl-4-piperidinyl 3-oxo-2-diazostearate
(5) Diphenylphosphine-oxide-diazoacetic acid (2,2,6,6-tetramethyl-4-piperidinyl)-amide
(6) 2,2,6,6-Tetramethyl-4-piperidinyl diethylphosphonodiazoacetate
(7) 1,2,2,6,6-Pentamethyl-4-piperidinyl 4-methyl-phenylsulphone-diazoacetate
(8) β-(2,2,6,6-Tetramethyl-1-piperidinyl)-ethyl tert.nonylsulphone-diazoacetate
(9) 2,2,6,6-Tetramethyl-4-piperidinyl 3,5-di-tert.butyl-4-hydroxybenzylsulphone-diazoacetate
(10) 1,2,2,6,6-Pentamethyl-4-piperidinyl octylsulphone-diazoacetate

(11) 2,2,6,6-Tetramethyl-4-piperidinyl 3,3-bis-(3-tert.butyl-4-hydroxyphenyl)-1-methyl-propylsulphone-diazoacetate

(12) 1-Acetyl-2,2,6,6-tetramethyl-4-piperidinyl α-diazocyanoacetate

(13) Di-(1-octyl-2,2,6,6-tetramethyl-4-piperidinyl) diazomalonate.

Suitable polymers which can be stabilised, by the process proposed here, against light degradation are preferably those polymers which contain aliphatic CH, $CH_2$ or $CH_3$ groups. These include, for example:

1. Polymers of monoolefines and diolefines, for example polyethylene (which optionally can be crosslinked), polypropylene, polyisobutylene, polymethylbutene-1, polymethylpentene-1, polyisoprene or polybutadiene.

2. Mixtures of the polymers mentioned under (1), for example mixtures of polypropylene with polyethylene or with polyisobutylene.

3. Copolymers of monoolefines and diolefines, such as, for example, ethylene/propylene copolymers, propylene/butene-1 copolymers, propylene/isobutylene copolymers, ethylene/butene-1 copolymers and also terpolymers of ethylene with propylene and a diene, such as hexadiene, dicyclopentadiene or ethylidenenorbornene.

4. Polystyrene.

5. Copolymers of styrene or α-methylstyrene, such as, for example, styrene/butadiene, styrene/acrylonitrile, styrene/acrylonitrile/methyl acrylate; mixtures, of high impact strength, of styrene copolymers and another polymer, such as, for example, a polyacrylate, a diene polymer or an ethylene/propylene/diene terpolymer; and block copolymers of styrene, such as, for example, styrene/butadiene/styrene, styrene/isoprene/styrene or styrene/ethylene/butylene/styrene.

6. Graft copolymers of styrene, such as, for example, styrene on polybutadiene, styrene and acrylonitrile on polybutadiene and mixtures thereof with the copolymers mentioned under (5), such as are known as so-called ABS polymers.

7. Halogen-containing polymers, such as, for example, polyvinyl chloride, polyvinylidene chloride, polyvinyl fluoride, polychloroprene, chlorinated rubbers and copolymers, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polyacrylamides and polyacrylonitrile.

9. Polymers which are derived from unsaturated alcohols and amines or acyl derivatives or acetals thereof, such as polyvinyl alcohol, polyvinyl acetate, polyvinyl stearate, polyvinyl benzoate, polyvinyl maleate, polyvinylbutyral, polyallyl phthalate, polyallyl-melamine and copolymers thereof with other vinyl compounds, such as ethylene/vinyl acetate copolymers.

10. Homopolymers and copolymers of epoxides, such as polyethylene oxide, polypropylene oxide or polyisobutylene oxide.

11. Polyacetals, such as polyoxymethylene and those polyoxymethylenes which contain ethylene oxide as a comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactams, such as polyamide 6, polyamide 6/6, polyamide 6/10, polyamide 11, polyamide 12 or poly-m-phenyleneisophthalamide.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylol-cyclohexane terephthalate.

18. Crosslinked polymers which are derived from aldehydes on the one hand and phenols, ureas and melamines on the other hand, such as phenol/formaldehyde resins, urea/formaldehyde resins and melamine/formaldehyde resins.

19. Alkyd resins, such as glycerol/phthalic acid resins and mixtures thereof with melamine/formaldehyde resins.

20. Unsaturated polyester resins which are derived from copolyesters of saturated and unsaturated dicarboxylic acids with polyhydric alcohols and vinyl compounds as crosslinking agents.

21. Crosslinked epoxide resins which are derived from polyepoxides, for example from bis-glycidyl ethers or from cycloaliphatic diepoxides.

22. Natural polymers, such as cellulose, rubber, proteins and derivatives thereof which are chemically modified in a polymer-homologous manner, such as cellulose acetates, cellulose propionates and cellulose butyrates, or cellulose ethers, such as methylcellulose.

Amongst these polymers, groups 1–6 should be singled out since these are particularly readily accessible to the coupling reaction and normally are extensively degraded by light. The stabilisation, according to the invention, of polyolefines is of particular importance.

The amounts of diazo compounds of the formula I, which are added to the polymer and are to be bonded to the latter by heating or exposure to light, in order to ensure long-lasting light stablisation, are about 0.01 to 1% by weight, calculated on the material to be stabilised. Preferably 0.1 to 0.5% by weight are used.

The diazo compound can be mixed with the polymer in a dry form or in solution or suspension. Alternatively, the powdered or granulated polymer is coated with a solution of the diazo compound. An addition during the manufacture of the polymer is also possible, that is to say the diazo compound is added to the monomer or the prepolymer. This frequently applies, for example in the case of lacquers and coatings, or in the case of resins which are cured so as to cause crosslinking. In this case the diazo compound is thus admixed to the prepolymer (or the solution thereof) and, during the heat-curing or photochemical curing, coupling of the stabiliser to the resin occurs simultaneously. Examples of which the coupling of the stabiliser is advantageously effected photochemically, are UV-curable lacquers and coatings or films and coatings which have been manufactured by a cold method.

The polymers stabilised in this way can also contain other known stabilisers, for example those which are listed in DT-OS No. 2,349,962, pages 25–32. When such known stabilisers are used additionally, synergistic effects can arise. The additional use of antioxidants is of particular importance, especially for polyolefines. Moreover, other additives which are customary in plastics technology can also be used additionally, such as, for example, plasticisers, lubricants, pigments, fillers, glass fibres, flame-proofing agents or antistatic agents.

The invention is explained in more detail by the examples which follow, without being limited thereto. In the examples, parts denote parts by weight and percentages denote percentages by weight.

EXAMPLES 1 and 2

19.1 g (0.05 mol) of bis-(2,2,6,6-tetramethyl-4-piperidinyl) malonate, 9.9 g (0.05 mol) of tosyl azide and 7.1 ml of triethylamine in 85 ml of acetonitrile are stirred at room temperature for 24 hours. Subsequently, the acetonitrile is distilled off in vacuo at 30°–35°. The residue is extracted with 2 N HCl, insoluble matter is separated off and the aqueous phase is neutralised with 2 N NaOH. The product which has thus precipitated is filtered off and recrystallised from aqueous methanol. The resulting bis-(2,2,6,6-tetramethyl-4-piperidinyl) diazomalonate (compound No. 1) melts at 98° C.

If bis-(1,2,2,6,6-pentamethyl-4-piperidinyl) malonate is used and the procedure followed is as described above, bis-(1,2,2,6,6-pentamethyl-4-piperidinyl) diazomalonate (compound No. 2) of melting point 98° C. is obtained.

EXAMPLE 3

A solution of 11 g of 1,2,2,6,6-pentamethyl-4-piperidinyl acetoacetate (0.04 mol) and 7.9 g of tosyl azide (0.04 mol) in 100 ml of methylene chloride is vigorously stirred with 13.5 ml of 3 N NaOH and 0.4 g of a cationic wetting agent (Aliquat 336, Fluka AG). After 18 hours, the organic phase is separated off, washed with water and dried over $MgSO_4$. The solvent is distilled off under reduced pressure and the residue is purified by column chromatography over 150 g of silica gel. This gives, as the main fraction, 8.5 g of 1,2,2,6,6-pentamethyl-4-piperidinyl α-diazo-acetoacetate (compound No. 3) in the form of a yellow oil.

EXAMPLE 4

Analogously to Example 3, 9.6 g of 2,2,6,6-tetramethyl-4-piperidinyl t-butylsulphoneacetate (0.03 mol) and 5.9 g of tosyl azide (0.03 mol) in 100 ml of methylene chloride are reacted with 6 ml of 10 N NaOH and 0.2 g of Aliquat 336. After analogous working up and purification by column chromatography, 6.5 g of 2,2,6,6-tetramethyl-4-piperidinyl α-diazo-t-butylsulphoneacetate (compound No. 4) of melting point 70° C. are obtained.

EXAMPLE 5

A solution of 35.0 g of 1,2,2,6,6-pentamethyl-4-piperidinyl diethyl-phosphonoacetate in 50 ml of benzene is added dropwise under nitrogen to a suspension of 12.2 g of potassium-t-butylate in 50 ml of abs. benzene, and refluxing is performed for 10 minutes. An addition of 19.7 g of p-toluenesulphonic acid azide, dissolved in 50 ml of benzene, is made dropwise at 5°–10° in the course of 15 minutes, and the yellow suspension is stirred for 3 hours at room temperature. It is washed with 100 ml of water; the aqueous phase is then extracted three times with 50 ml of ether each time, and the combined organic phases are washed with 100 ml of 2 N NaOH. From the organic phase are obtained, after drying over $MgSO_4$ and removal of the solvent by distillation, 43.2 g of yellow oil, which is chromatographed on silica gel. After elution with about 1.5 liters of petroleum ether/ether for separation of the unreacted sulphonyl azide, there remain 29.0 g of 1,2,2,6,6-pentamethyl-4-piperidinyl α-diazo-diethyl-phosphonoacetate as a yellowish liquid; IR: 2142 (N≡N) $cm^{-1}$; analysis: calculated: N, 11.19%; found: N, 10.92%.

EXAMPLES 6 to 10

10.0 g of tosyl azide are added to a solution of 13.6 g of monomethyl-mono-(1,2,2,6,6-pentamethyl-4-piperidinyl)-malonate and 5.2 g of triethylamine in 85 ml of acetonitrile. The clear solution is stirred for 22 hours at room temperature and subsequently concentrated by evaporation in vacuo. The residue is taken up in 100 ml of ether and the solution obtained is washed with 100 ml of 30% KOH. The ether phase is dried over $MgSO_4$ and concentrated by evaporation. There remain 15.1 g of a yellow oil, which is purified by chromatography on silica gel. There are obtained 7.9 g of pure monomethyl-mono-(1,2,2,6,6-pentamethyl-4-piperidinyl)-diazomalonate (compound No. 6); IR: 2137 (N≡N) $cm^{-1}$; analysis: calculated: C, 56.55; H, 7.80; N, 14.13%; found: C, 56.40; H, 7.85; N, 13.52%.

The following compounds are obtained analogously:
bis-[2-(2',2',6',6'-tetramethyl-1'-piperidinyl)-ethyl]-diazomalonate (compound No. 7); IR: 2132 (N≡N) $cm^{-1}$; analysis: calculated: N, 12.06%; found: N, 11.68%;

monomethyl-mono-(1-allyl-2,2,6,6-tetramethyl-4-piperidinyl)-diazomalonate (compound No. 8); IR: 2150 (N≡N) $cm^{-1}$; analysis: calculated: N, 13.00%; found: N 12.59%;

bis-(1-allyl-2,2,6,6-tetramethyl-4-piperidinyl)-diazomalonate (compound No. 9); IR: 2138 (N≡N) $cm^{-1}$;

bis-(1-propyl-2,2,6,6-tetramethyl-4-piperidinyl)-diazomalonate (compound No. 10); IR: 2150 (N≡N) $cm^{-1}$; analysis: calculated: N, 11.37%; found: N, 11.30%.

EXAMPLE 11

A solution of 0.7 g of sodium in 20 ml of methanol is slowly added dropwise at 0° C. to 7.2 g of 1,2,2,6,6-pentamethyl-4-piperidinyl diazoacetoacetate in 30 ml of methanol. The mixture is stirred at 0° for one hour and then poured onto 200 ml of ice water. It is extracted three times with 50 ml of petroleum ether each time, dried over $MgSO_4$ and concentrated by evaporation. After purification by chromatography through silica gel there remain 2.2 g of 1,2,2,6,6-pentamethyl-4-piperidinyl diazoacetate as yellow oil (compound No. 11); IR: 2119 (N≡N) $cm^{-1}$; analysis: calculated: C, 60.23; H, 8.85; N, 17.56%; found: C, 60.28; H, 8.61; N, 16.77%.

EXAMPLES 12 to 16

If the procedure is carried out as described in Example 1 but with use of the following starting materials:
(a) bis-(1-benzyl-2,2,6,6-tetramethyl-4-piperidinyl)-malonate,
(b) malonic acid-bis-(2,2,6,6-tetramethyl-4-piperidinyl)-amide,
(c) bis-(2,3,6-trimethyl-2,6-diethyl-4-piperidinyl)-malonate,
(d) bis-[2-(2,2,6,6-tetramethyl-4-benzoyloxy-1-piperidinyl)-ethyl]-malonate, and
(e) malonic acid-mono-(1,2,2,6,6-pentamethyl-4-piperidinyl)-ester-mono-tert.-octylamide,
there are obtained the following diazo compounds respectively:

(a) bis-(1-benzyl-2,2,6,6-tetramethyl-4-piperidinyl)-diazomalonate, m.p. 130°–132° C. (compound No. 12), (b) diazo-malonic acid-bis-(2,2,6,6-tetramethyl-4-piperidinyl)-amide, m.p. 148°–150° C. (compound No. 13), (c) bis-(2,3,6-trimethyl-2,6-diethyl-4-piperidinyl)-diazomalonate as an oily residue (calculated:, C 65.82%, found: C, 66.97%) (compound No. 14), (d) bis-[2-(2,2,6,6-tetramethyl-4-benzoyloxy-1-piperidinyl)-ethyl]-diazomalonate, after chromatography, as a yellowish oil (compound No. 15), and (e) diazomalonic acid-mono-(1,2,2,6,6-pentamethyl-4-piperidinyl)-ester-mono-tert.-octylamide, m.p. 126° C. (compound No. 16).

EXAMPLE 17

100 parts of polypropylene powder (Moplen, fibre grade, from Messrs. Montedison) are homogenised with 0.2 part of octadecyl β-(3,5-di-tert.butyl-4-hydroxyphenyl)-propionate and 0.25 part of a stabiliser from the table which follow, at 200° C. for 10 minutes in a Brabender plastograph. The composition thus obtained is withdrawn as rapidly as possible from the kneader and pressed in a toggle press to give a sheet 2-3 mm thick. A part of the raw pressing obtained is cut out and pressed between two high-gloss hard aluminium foils, by means of a manual hydraulic laboratory press, at 260° C. under a pressure of 12 tonnes for 6 minutes, to give a film 0.5 mm thick which is immediately quenched in cold water. The 0.1 mm thick test film is prepared from this 0.5 mm film under exactly the same conditions. Sections of 60×44 mm each are then punched from this test film and exposed in a Xenotest 150. These test specimens are withdrawn from the exposure apparatus at regular intervals and tested in a IR spectrophotometer for their carbonyl content. The increase in the carbonyl extinction at 5.85μ during exposure is a measure for the photo-oxidative degradation of the polymer (see L. Balaban et al., J. Polymer Sci, Part C, 22, 1,059–1,071 (1969)) and, as experience shows, is related to a deterioration in the mechanical properties of the polymer. The time until a carbonyl extinction of about 0.3 is reached, at which point the comparison film is brittle, is taken as a measure of the protective action.

The protective action of the stabilisers according to the invention can be seen from the table which follows:

Table

| Compound No. | Exposure time in hours up to a carbonyl extinction of 0.300 |
|---|---|
| without light stabiliser | 1050 |
| 1 | 14170 |
| 2 | 11190 |
| 12 | <3000 |

What is claimed is:

1. A diazo compound of the formula

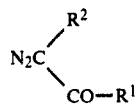

in which $R^1$ is a radical of the formula

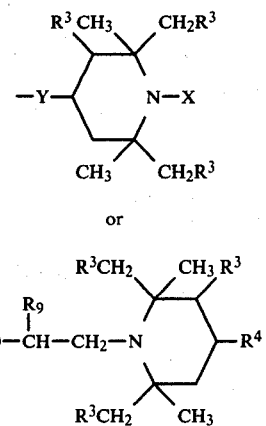

and $R^2$ represents hydrogen —CHO, —CN, —NO$_2$, —COR$^1$, —COR$^5$, —SO$_2$R$^6$, —COOR$^7$, —CONH$_2$, —CONHR$^{17}$, —CON(R$^{17}$)$_2$, —P(O)(C$_6$H$_5$)$_2$ or —P(O)(OR$^{18}$)$_2$, X denotes H, O, alkyl with 1–12 C atoms, alkenyl with 3–6 C atoms, alkinyl with 3–6 C atoms, alkoxyalkyl with 3–10 C atoms, phenylalkyl with 7–9 C atoms, 2,3-epoxypropyl —CH$_2$ COOR$^8$, —CH$_2$CH$_2$COOR$^8$, —CH$_2$CH(R$^9$)—OR$^{10}$, —COR$^{11}$, —COOR$^{12}$ or —CONHR$^{13}$, Y denotes oxygen, NH or N-alkyl with 1–4 C atoms, R$^3$ denotes H or alkyl with 1–4 C atoms, R$^4$ denotes, H, —OR$^{14}$ or —N(R$^{15}$)(R$^{16}$), R$^5$ and R$^6$ denote alkyl with 1–18 C atoms, cyclohexyl, aryl with 6–10 C atoms, aryl with 6–10 C atoms substituted by chlorine or alkyl with 1–8 C atoms, phenylalkyl with 7–9 C atoms phenylalkyl with 7–9 C atoms substituted by one or two alkyl with 1–4 C atoms or by hydroxyl or combinations thereof, or a group of the formula —CH$_2$COR$^1$ or —CH$_2$COOR$^{12}$, R$^7$ denotes alkyl with 1–18 C atoms, alkenyl with 3–6 C atoms, alkinyl with 3–6 C atoms, cycloalkyl with 5–12 C atoms, phenyl, alkylphenyl with 7–14 C atoms or phenylalkyl with 7–9 C atoms, R$^8$ denotes alkyl with 1–18 C atoms, alkenyl with 3–6 C atoms, phenyl, benzyl or cyclohexyl, R$^9$ denotes H, methyl or phenyl, R$^{10}$ denotes, H, C$_1$–C$_{18}$ alkyl, C$_5$–C$_{12}$ cycloalkyl, C$_7$–C$_{14}$ aralkyl, C$_3$–C$_6$ alkenyl, C$_3$–C$_6$ alkenyl or an aliphatic acyl, aromatic acyl, araliphatic acyl or cycloaliphatic acyl each acyl group derived from a monocarboxylic acid with up to 18 C atoms, wherein the aromatic part can be substituted by halogen, alkoxy or alkyl each with 1–4 C atoms or hydroxyl or combinations thereof, R$_{11}$ denotes H, alkyl with 1–6 C atoms or alkenyl with 2–4 C atoms, R$^{12}$ denotes alkyl with 1–12 C atoms, phenyl, benzyl or cyclohexyl, R$^{13}$ denotes alkyl with 1–12 C atoms, aryl with 6–10 C atoms, aryl with 6–10 C atoms substituted by chlorine or alkyl with 1–8 C atoms, phenylalkyl with 7–9 C atoms or cyclohexyl, R$^{14}$ denotes alkyl with 1–18 C atoms, alkenyl with 3–6 C atoms, alkinyl with 3–6 C atoms, benzyl, 2-cyanoethyl, an aliphatic acyl, cycloaliphatic acyl, aromatic acyl or araliphatic acyl each aryl group derived from a monocarboxylic acid with up to 18 C atoms, which can be substituted in the aromatic part by halogen, alkyl or alkoxy each with 1–4 C atoms or hydroxyl or combinations thereof, R$^{15}$ denotes alkyl with 1–18 C atoms, alkenyl with 3–6 C atoms or phenylalkyl with 7–9 C atoms, R$^{16}$ denotes an aliphatic acyl, cycloaliphatic acyl, aromatic acyl or araliphatic acyl each acyl group derived from a monocarboxylic acid with up to 18 C atoms, which can be substituted in the aromatic part by halogen, alkyl or alkoxy each with 1–4

C atoms or hydroxyl or combinations thereof, $R^{17}$ denotes alkyl with 1-12 C atoms, cyclohexyl, benzyl or phenyl and $R^{18}$ denotes alkyl with 1-18 C atoms, aryl with 6-10 C atoms, aryl with 6-10 C atoms substituted by chlorine or alkyl with 1-8 C atoms, or phenyl-alkyl with 7-9 C atoms.

2. A compound according to claim 1, in which $R^3$ denotes hydrogen or methyl.

3. A compound according to claim 1 in which $R^3$ denotes hydrogen.

4. A compound according to claim 1 in which $R^1$ is a radical of the formula,

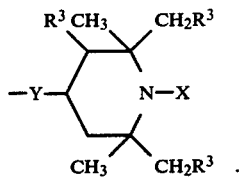

wherein X represents hydrogen, alkyl with 1-8 C atoms, allyl, benzyl or one of the groups —$CH_2COOR^8$, —$CH_2CH_2COOR^8$, —$CH_2CH_2OR^{10}$ or —$COR^{11}$ and $R^8$ denotes alkyl with 1-12 C atoms, $R^{10}$ denotes hydrogen or alkanoyl with 1-18 C atoms and $R^{11}$ denotes alkyl with 1-3 C atoms, vinyl or propenyl.

5. A compound according to claim 1 in which $R^1$ is a radical of the formula

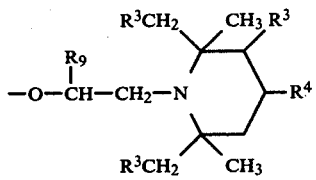

wherein $R^4$ represents hydrogen or —$OR^{14}$ and $R^{14}$ represents an aliphatic acyl with 1-18 C atoms or benzoyl.

6. A compound according to claim 1 in which $R^2$ is hydrogen, —CN, —$COR^1$, —$COR^5$, —$SO_2R^6$ or —$COOR^7$, wherein $R^5$ denotes alkyl with 1-8 C atoms, phenyl, 4-hydroxy-3,5-di-tert.butyl-phenyl or 2-(4-hydroxy-3,5-di-tert.butylphenyl)-ethyl, $R^6$ denotes alkyl with 1-12 C atoms, phenyl or 4-hydroxy-3,5-di-tert.butyl-benzyl and $R^7$ denotes alkyl with 1-18 C atoms.

7. A compound according to claim 1 in which $R^1$ is a radical of the formula

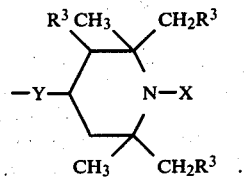

wherein $R^3$ is hydrogen, X is hydrogen or methyl and Y is oxygen.

8. A compound according to claim 1 in which $R^1$ is a radical of the formula

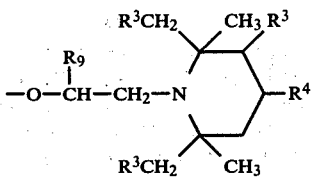

wherein $R^3$ and $R^4$ are hydrogen.

9. A compound according to claim 7 in which $R^2$ is hydrogen, —CN, —$COR^1$, —$COR^5$ or —$COOR^7$, $R^5$ denotes alkyl with 1-6 C atoms or phenyl and $R^7$ denotes alkyl with 1-4 C atoms.

10. A compound according to claim 8 in which $R^2$ is hydrogen, —CN, —$COR^1$, —$COR^5$ or —$COOR^7$, $R^5$ denotes alkyl with 1-6 atoms or phenyl and $R^7$ denotes alkyl with 1-4 C atoms.

11. The compound according to claim 1, bis-(2,2,6,6-tetramethyl-4-piperidinyl)-diazomalonate.

12. The compound according to claim 1, bis-(1,2,2,6,6-pentamethyl-4-piperidinyl)-diazomalonate.

13. A composition of matter stabilized against UV light degradation which comprises an organic polymeric material normally subject to UV light degradation containing from 0.1 to 1% by weight of at least one diazo compound according to claim 1.

14. A polymer according to claim 13, which is a polymer of mono or diolefins.

* * * * *